(12) United States Patent
Connelly et al.

(10) Patent No.: US 9,134,237 B2
(45) Date of Patent: Sep. 15, 2015

(54) HIGH SENSITIVITY MULTIPARAMETER METHOD FOR RARE EVENT ANALYSIS IN A BIOLOGICAL SAMPLE

(75) Inventors: Mark Carle Connelly, Doylestown, PA (US); Frank Coumans, Stein (NL); Steve Gross, Ambler, PA (US); Mike Kelly, Coatesville, PA (US)

(73) Assignee: Janssen Diagnotics, LLC, Raritan, NJ (US)

( * ) Notice: Subject to any disclaimer, the term of this patent is extended or adjusted under 35 U.S.C. 154(b) by 541 days.

(21) Appl. No.: 12/181,399

(22) Filed: Jul. 29, 2008

(65) Prior Publication Data

US 2009/0029378 A1 Jan. 29, 2009

Related U.S. Application Data

(63) Continuation-in-part of application No. 12/067,532, filed as application No. PCT/US2006/036656 on Sep. 20, 2006.

(60) Provisional application No. 60/718,676, filed on Sep. 20, 2005, provisional application No. 60/729,536, filed on Oct. 24, 2005, provisional application No. 60/786,117, filed on Mar. 27, 2006.

(51) Int. Cl.
| | |
|---|---|
| *G01N 33/574* | (2006.01) |
| *G01N 33/53* | (2006.01) |
| *C12N 5/07* | (2010.01) |
| *G01N 33/566* | (2006.01) |
| *G01N 33/553* | (2006.01) |
| *G01N 21/64* | (2006.01) |
| *G01N 33/50* | (2006.01) |
| *G01N 33/569* | (2006.01) |
| *G01N 33/58* | (2006.01) |

(52) U.S. Cl.
CPC ........ *G01N 21/6428* (2013.01); *G01N 21/6458* (2013.01); *G01N 33/5091* (2013.01); *G01N 33/5094* (2013.01); *G01N 33/569* (2013.01); *G01N 33/57488* (2013.01); *G01N 33/582* (2013.01); *G01N 2021/6441* (2013.01)

(58) Field of Classification Search
USPC ........ 435/7.1, 7.23, 334; 422/82.07; 436/501, 436/526
See application file for complete search history.

(56) References Cited

U.S. PATENT DOCUMENTS

| | | | | |
|---|---|---|---|---|
| 5,821,066 | A * | 10/1998 | Pyle et al. ........................ | 435/7.2 |
| 6,150,173 | A | 11/2000 | Schubert | |
| 6,169,169 | B1 | 1/2001 | Hyldig-Nielsen et al. | |
| 6,365,362 | B1 | 4/2002 | Terstappen et al. | |
| 6,429,293 | B1 | 8/2002 | Hew | |
| 6,541,204 | B2 | 4/2003 | Nilsen et al. | |
| 2002/0098535 | A1 | 7/2002 | Wang et al. | |
| 2002/0109838 | A1 | 8/2002 | Columbus et al. | |
| 2002/0172987 | A1* | 11/2002 | Terstappen et al. .......... | 435/7.23 |
| 2003/0082632 | A1 | 5/2003 | Shumate | |
| 2003/0119077 | A1 | 6/2003 | Ts'o et al. | |
| 2003/0124530 | A1 | 7/2003 | Edwards et al. | |
| 2003/0129626 | A1 | 7/2003 | Nielsen et al. | |
| 2004/0209298 | A1 | 10/2004 | Kamberov et al. | |
| 2005/0064450 | A1 | 3/2005 | Lucas et al. | |
| 2005/0164216 | A1 | 7/2005 | Lukyanov et al. | |
| 2008/0003610 | A1* | 1/2008 | Frank et al. ........................ | 435/6 |
| 2008/0094614 | A1* | 4/2008 | Tuschel et al. .................. | 356/73 |

FOREIGN PATENT DOCUMENTS

| | | |
|---|---|---|
| CN | 1494552 A | 4/2006 |
| EP | 1722230 A2 | 11/2006 |
| JP | 2000508171 A | 10/1997 |
| JP | 2003527098 A | 3/2001 |
| JP | 2002-517183 A | 6/2002 |
| JP | 2005507997 A | 5/2003 |
| JP | 2005-524833 A | 8/2005 |
| JP | 2007-505626 A | 3/2007 |
| JP | 2005522224 A | 7/2009 |
| JP | 2005514062 A | 11/2010 |
| WO | WO 01/06014 | 1/2001 |
| WO | WO 2004/058404 A2 | 7/2004 |
| WO | WO 2004/076643 A2 | 9/2004 |

(Continued)

OTHER PUBLICATIONS

Mittag et al, Hyperchromatic cytometry principle for cytomics using a slide based cytometry, 2006, Cytometry Part A, 69A, 691-703.*
Laffers et al, Iterative restaining as a pivotal tool for n-color immunophenotyping by slide based cytometry, 2006, Cytometry Part A, 69A, 127-130.*
de Bono et al, Potential Applications for Circulating Tumor Cells Expressing the Insulin-Like Growth Factor-I Receptor, 2007, Clin Cancer Res, 13:3611-3616.*
Craig, J., et al. "Removal of Repetitive Sequences from FISH Probes Using PCR-Assisted Affinity Chromatography", Human Genetics, vol. 100, pp. 472-476 (1997).

(Continued)

*Primary Examiner* — Narayan Bhat

(57) ABSTRACT

A sample of blood containing CTCs, or other cells of interest, is stained with fluorescent markers for image analysis and scanned to identify the presence and location within the cartridge of target cells or subcellular elements. A sample containing desired target cells or subcellular elements is then further processed, in part by photobleaching the sample, so that those same targets may be re-analyzed with additional biomarkers conjugated to the same or different fluorochromes using the same imaging criteria that were used for the initial analysis. The present invention has applications with targets such as circulating epithelial, cells, circulating tumor cells, circulating endothelial cells, leukocytes, lymphocyte subsets, cells containing an organelle or receptor of interest, cellular debris, disrupted cells and their debris, or any other formed element that might be captured and imaged. The invention provides a means to further interrogate individual targets of interest, especially when coupled with genetic analysis such as FISH.

6 Claims, 6 Drawing Sheets

(56) References Cited

FOREIGN PATENT DOCUMENTS

| WO | WO 2004/083386 | | 9/2004 |
|---|---|---|---|
| WO | WO2007/053245 | * | 5/2007 |
| WO | WO 2007/053245 A2 | | 5/2007 |

OTHER PUBLICATIONS

Office Action/Reasons for Rejection dated Dec. 6, 2011 for corresponding Japanese Patent Application No. JP-2008-532351.
Berndt, Uta et al., "Systematic high-content proteomic analysis reveals substantial immunologic changes in colorectal cancer," Cancer Research, vol. 68, No. 3, Feb. 2008, pp. 880-888.
Schubert, Walter et al., "Analyzing proteome topology and function by automated multidimensional fluorescence microscopy," Nature Biotechnology, Nature Publishing Group, NY, USA, vol. 24, No. 10, Oct. 2006, pp. 1270-1278.
Craig, J.M. et al., "Removal of Repetitive Sequcens from Fish Probes Using PCR-Assisted Affinity Chromatography," Human Genetics, Springer, Berlin, DE, vol. 100, Jan. 1997, pp. 472-476.
Davison, J.M. et al., "Technical advance. Subtracted unique sequence in situ hybridization experimental and diagnostic applications," American Journal of Pathology, American Society for Investigative Pathology, US, vol. 153, No. 5, Nov. 1998, pp. 1401-1409.
Anja Mittag et al., "Hyperchromatic cytometry principle for cytomics using a slide based cytometry" Cytometry Part A, 69A, No. 7, pp. 691-703 May 5, 2006.
Bonnekoh Bernd et al: "Profiling Lymphocyte Subpopulations in Peripheral Blood Under Efalizumab Treatment of Psoriasis by Multi Epitope Ligand Cartography (MELC) Robot Microscopy", European Journal of Dermatology, John Libbey Eurotext, FR, vol. 16, No. 6, Jan. 1, 2006, pp. 623-635, XP008079835, ISSN: 1167-1122.

* cited by examiner

Figure 1 Panel A
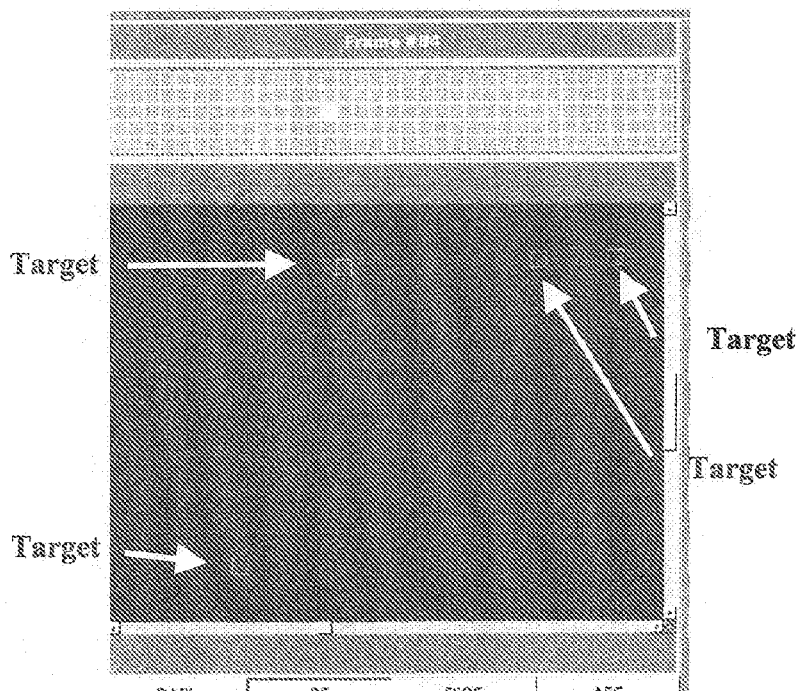
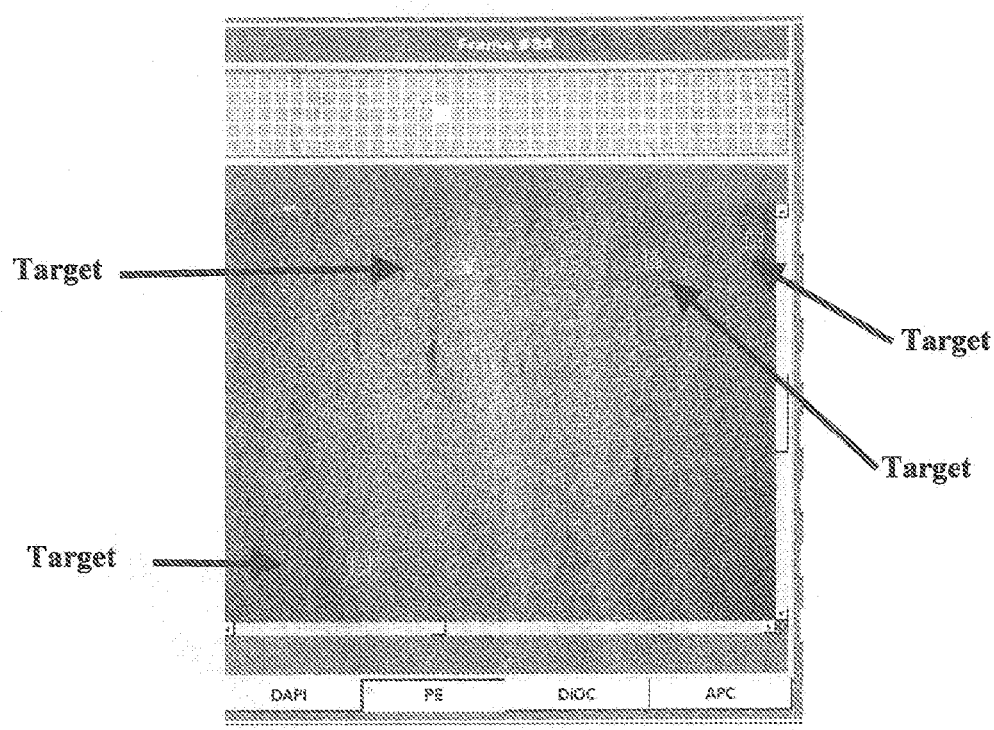

Figure 1 Panel B
Cells located before drying
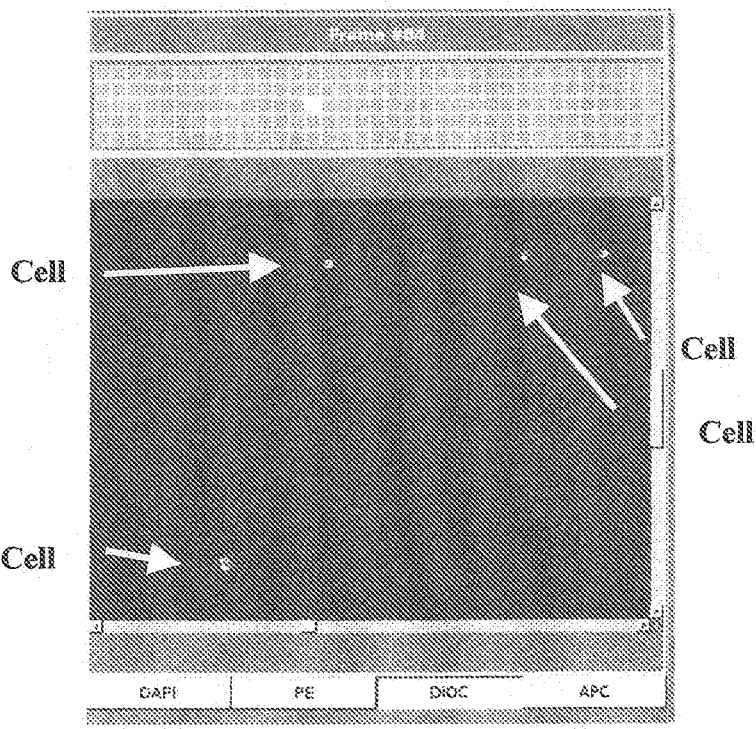
Cells located after drying
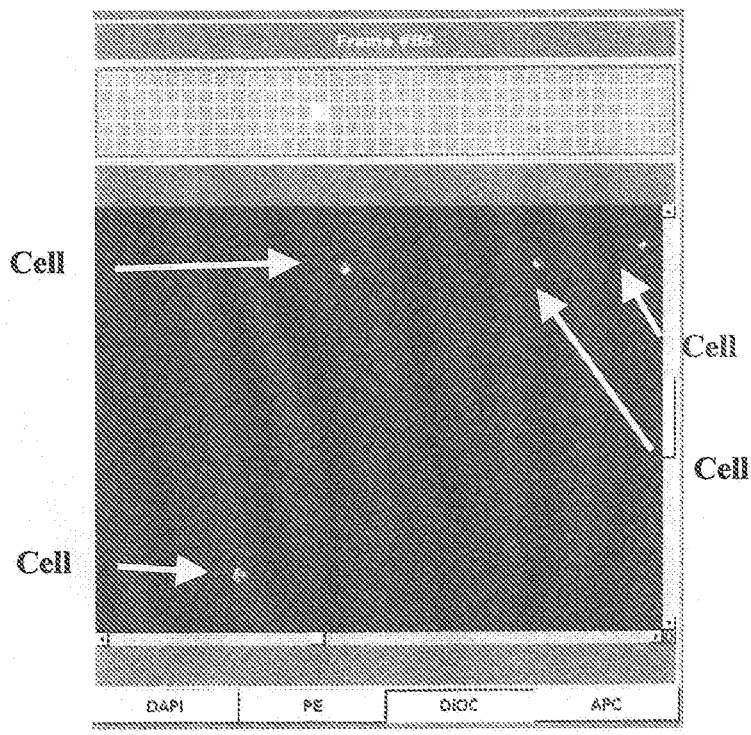

Figure 2
Sample processed on AutoPrep-Initial Scan
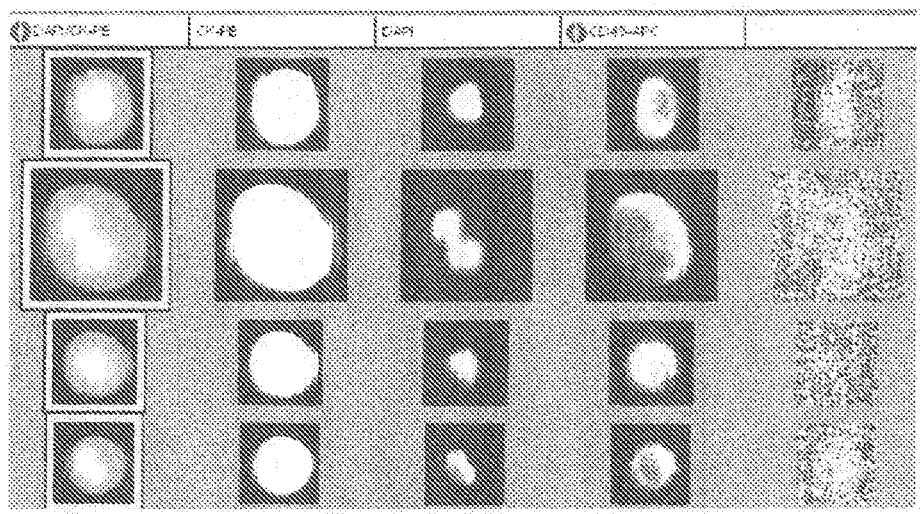
Sample re-stained in cartridge with C11-FITC
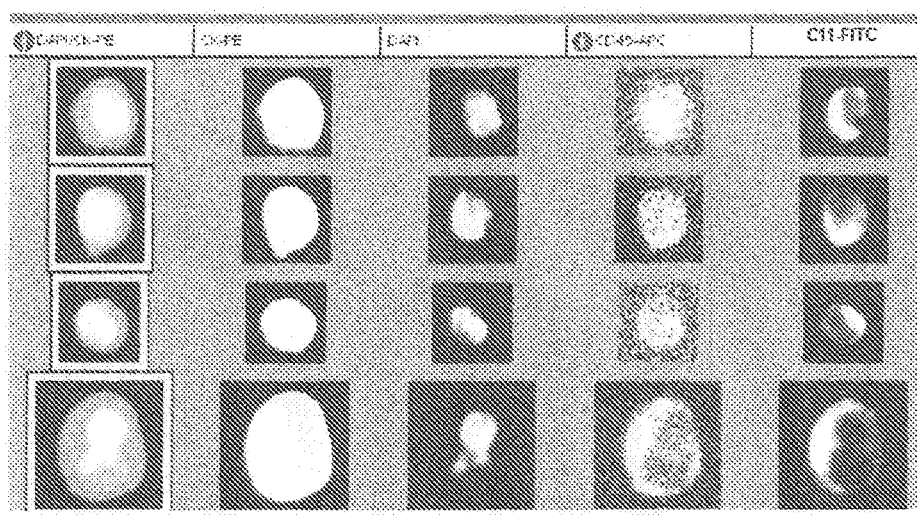

Figure 3 Panel A
Sample stained with C11-PE on AutoPrep-Initial Scan
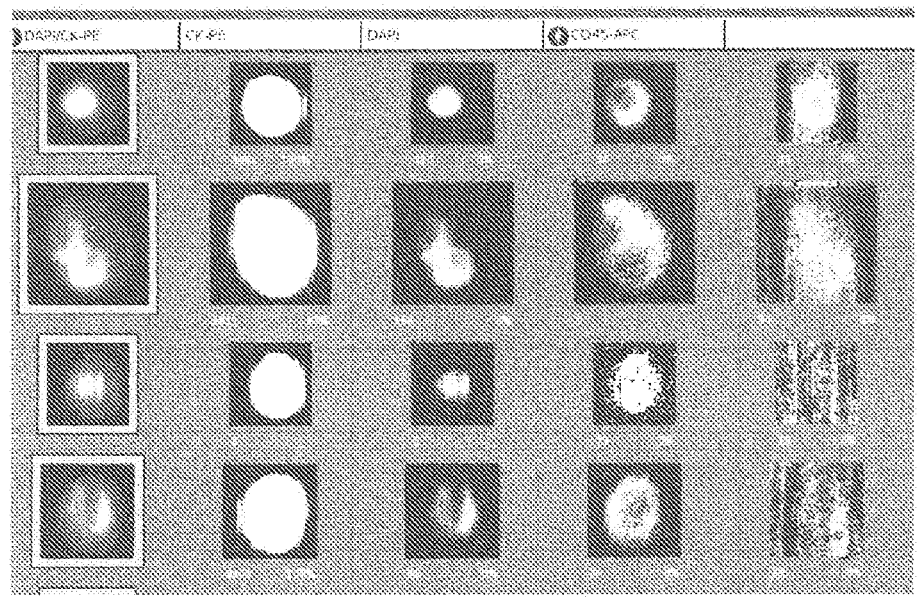
Sample bleached then re-stained with C11-FITC
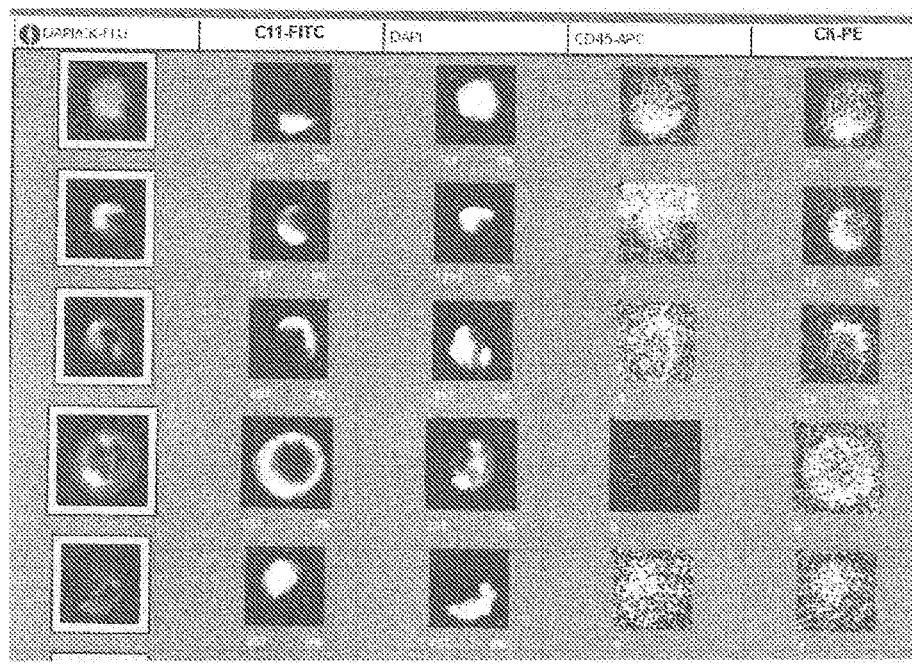

Figure 3 Panel B
Sample stained with C11-PE on AutoPrep-Initial Scan
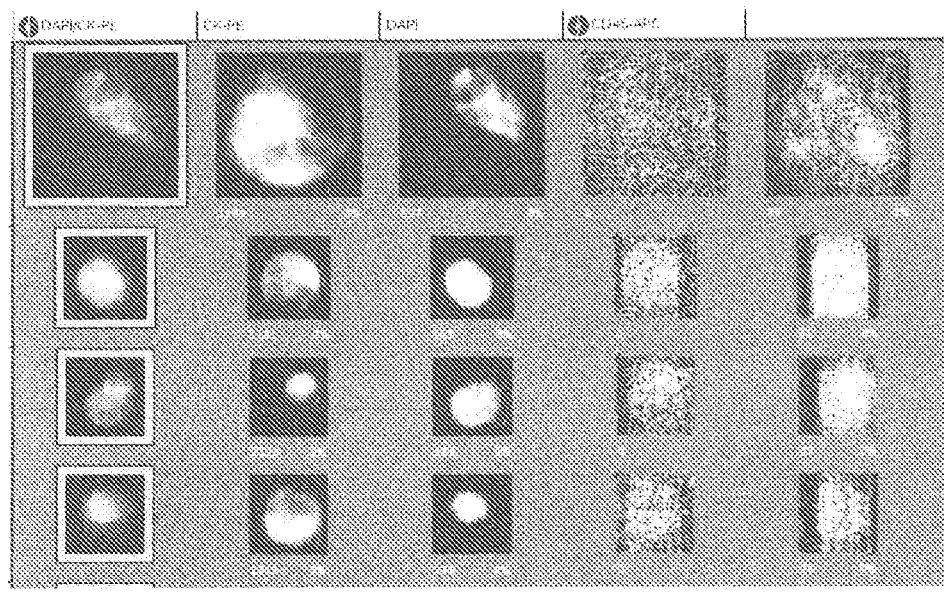
Sample bleached then re-stained with C11-FITC
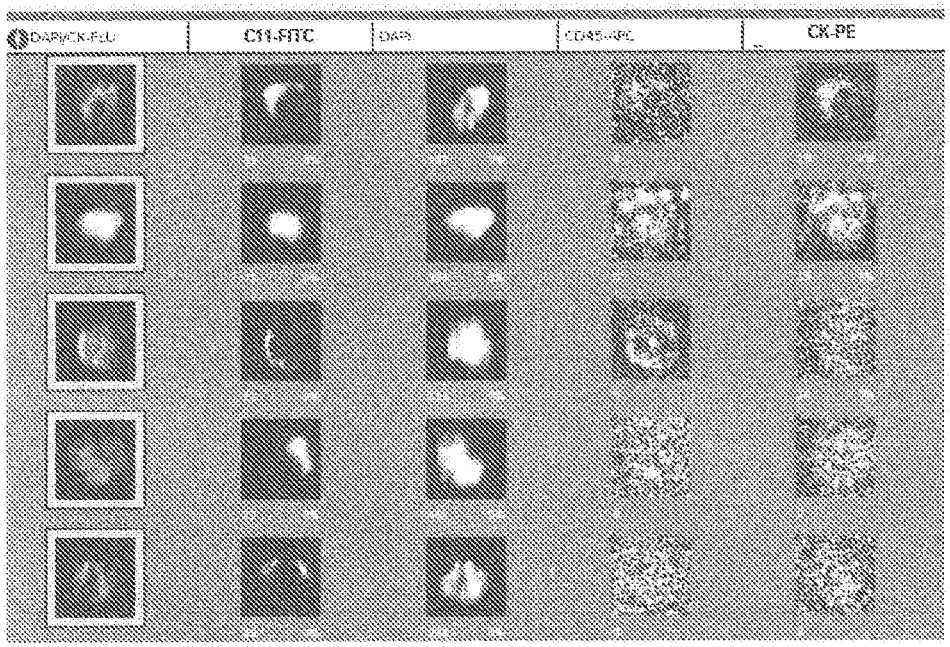

Figure 4 Panel A
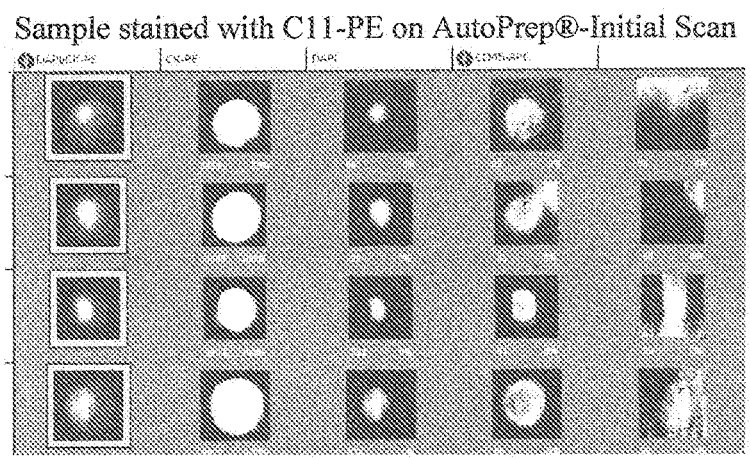
Sample stained with C11-PE on AutoPrep®-Initial Scan
Figure 4 Panel B
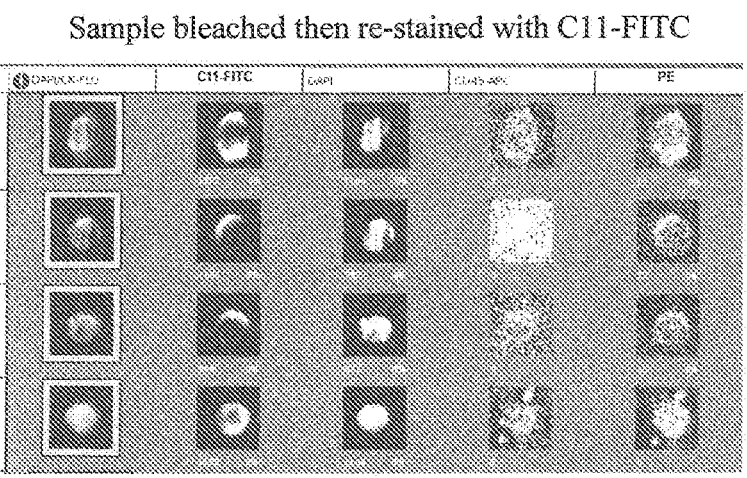
Sample bleached then re-stained with C11-FITC
Figure 4 Panel C
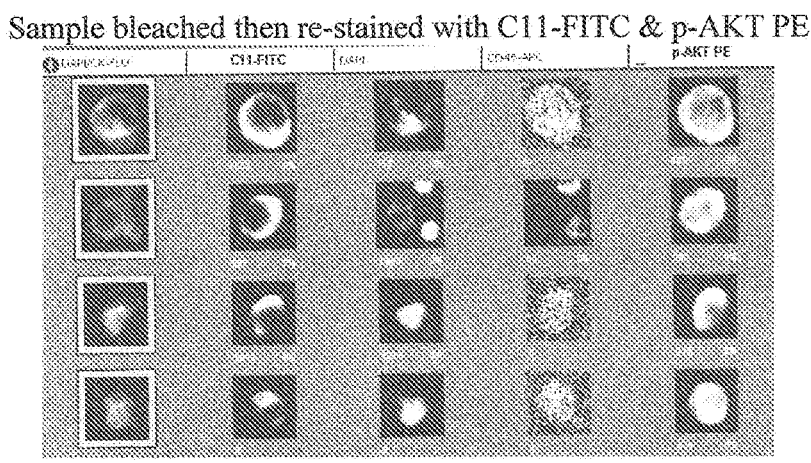
Sample bleached then re-stained with C11-FITC & p-AKT PE

HIGH SENSITIVITY MULTIPARAMETER METHOD FOR RARE EVENT ANALYSIS IN A BIOLOGICAL SAMPLE

CROSS-REFERENCE TO RELATED APPLICATIONS

This application is a continuation-in-part of U.S. application Ser. No. 12/067,532, filed 20 Mar. 2008 which claims priority to U.S. Provisional Applications 60/718,676, filed 20 Sep. 2005; 60/729,536, filed 24 Oct. 2005; and 60/786,117, filed March 2006. Each of the aforementioned applications is incorporated in full by reference herein.

BACKGROUND OF THE INVENTION

1. Field of the Invention

The invention relates to the fields of oncology and diagnostic testing. The invention is useful for screening, staging, treatment responses, recurrence or the like in diseases such as cancer or cardiovascular disorders. More specifically, the present invention provides methods which facilitate analysis and enumeration of circulating rare cells isolated from biological samples.

2. Background

Methods for the characterization of not only tumor cells, but also rare cells, or other biological entities from biological samples have been previously described (U.S. Pat. No. 6,365,362). This two stage method requires efficient enrichment to ensure acquisition of target cells while eliminating a substantial amount of debris and other interfering substances prior to analysis, allowing for cellular examination by imaging techniques. The method combines elements of immunomagnetic enrichment with multi-parameter flow cytometry, microscopy and immunocytochemical analysis in a uniquely automated way. The combination method is used to enrich and enumerate epithelial cells in blood samples, thus providing a tool for measuring cancer.

The two stage method has applications in cancer prognosis and survival for patients with metastatic cancer (WO 04076643). Based on the presence of morphologically intact circulating cancer cells in blood, this method is able to correlate the presence of circulating cancer cells of metastatic breast cancer patients with time to disease progression and survival. More specifically, the presence of five (5) or more circulating tumor cells per 7.5 milliliters provides a predictive value at the first follow-up, thus providing an early prognostic indicator of patient survival.

The specificity of the assay described above increases with the number of cells detected and is not sufficient in cases were only few (generally less than 5 circulating tumor cells) are detected. One solution to this problem is to provide detailed genetic information about suspected cancer cells. Accordingly, a method that would incorporate enrichment of a blood sample with multi-parametric image cytometry and multi-parametric genetic analysis on an individual suspect cancer cell would provide a complete profile and confirmatory mechanism to significantly improve current procedures for patient screening, assessing recurrence of disease, or overall survival. A confirmatory assay in the analysis of rare circulating cells by combining phenotypic and genotypic multiparametic analysis on an individually isolated target cell has been described (see pending U.S. application Ser. No. 12/067, 532). Confirmation provides for a clinically significant level of sensitivity and, therefore, assurance to the clinician of any quantitative information acquired. Relevant disease states are assessed using extremely small (1, 2, 3, or 4) numbers of circulating tumor cells (CTC's) and provide a confirmation for early disease detection.

There are no other technologies available that can perform multiple high sensitivity assays on the same sample with the same marker and do it on rare events. Multiparameter flow cytometry is commonly done, but it requires hundreds or thousands of target cells or events to get accurate information. However if a patient only has 6 CTCs in 7.5 mLs of blood there are too few events to even detect reliably, to say nothing of performing multiparameter analysis.

The present invention extends the enrichment and analysis protocol described in U.S. Pat. No. 6,365,362 and utilized in Celltracks® Autoprep® System and Celltracks® Analyzer II System (Immunicon Corporation, Huntingdon Valley, Pa.) by providing a means to allow for the interrogation of rare circulating cells with multiple fluorescent biomarkers

SUMMARY OF THE INVENTION

The invention described here consists of a method consisting of five parts working in conjunction to achieve the end result. The invention consists essentially of (1) Scanning a cartridge to identify those with target cells of interest and their location within the cartridge; (2) Aspirating the fluid from the cartridge to dry or actively fix the cells in their position on the cover slip; (3) Photobleaching the fluorescent signals to eliminate the fluorescence that was originally used to identify the target cell; (4) Restaining the cells within the cartridge with one or more fluorescent antibody conjugate(s) or dye(s) to label markers, receptors, proteins etc. of interest on or within the target of interest; (5) Rescan the cartridge and return to the previously identified targets of interest and determine if the cells are positive or negative for the desired markers or proteins.

A sample of blood containing CTCs, or other cells of interest, is stained with fluorescent markers for image analysis and scanned to identify the presence and location within the cartridge of target cells or subcellular elements. A sample containing desired target cells or subcellular elements is then further processed, in part by photobleaching the sample, so that those same targets may be re-analyzed with additional biomarkers conjugated to the same or different fluorochromes using the same imaging criteria that were used for the initial analysis. The present invention has applications with targets such as circulating epithelial, cells, circulating tumor cells, circulating endothelial cells, leukocytes, lymphocyte subsets, cells containing an organelle or receptor of interest, cellular debris, disrupted cells and their debris, or any other formed element that might be captured and imaged.

BRIEF DESCRIPTION OF THE DRAWINGS

FIG. 1: Panel A Confirmation of the integrity of the sample and location of the target after drying. Panel B Cells are shown at the same location before and after drying.

FIG. 2: Re-stained cartridge after drying.

FIG. 3: Bleaching of the fluorescent signal using LED's. Panel A Bleaching of SKBR cells stained with C11-PE followed by C11-FITC re-staining. Panel B Bleaching of PC3-9 cells stained with C11-PE followed by C11-FITC re-staining.

FIG. 4: Panel A shows the initial scan of SKBR Cells stained with C11-PE. Panel B shows the sample after bleaching and re-stain with C11-FITC alone. Panel C shows the sample re-stained with C11-FITC and pART-PE.

DETAILED DESCRIPTION OF THE INVENTION

Circulating tumor cells (CTCs) captured from blood have been detected and analyzed using CellTracks® Autoprep®

System and CellTracks® Analyzer II System (Immunicon Corporation, Huntingdon Valley, Pa.). In this procedure, a combination of fluorescent biomarkers and dyes are used to identify cells of epithelial origin and to distinguish them from contaminating leukocytes. The CellTracks® analysis platform is limited to four channels or colors to detect these fluorescent markers. A UV channel detects 4'-6'Diamidino-2-phenylindole (DAPI), a nuclear stain, to identify nucleated or cellular events; an allophycocyanin (APC) channel is used to detect CD45-APC which is used to identify leukocytes; and two marker channels, phycoerythrin (PE) and fluorescein isothiocyanate (FITC), are used to detect biomarkers conjugated to either PE or FITC. Using a standard CellSearch® kit (Veridex LLC, Raritan, N.J.) the PE is conjugated to cytokeratins which is used to identify epithelial cells and the FITC channel is available for additional markers of interest. The Epithelial Cell Kit (Immunicon Corporation, Huntingdon Valley, Pa.) uses the same combination of colors only the cytokeratin is now conjugated to FITC freeing the PE channel. The stronger signaling PE channel allows for the detection of dimmer biomarkers conjugated to PE.

Since only four channels or colors currently exist in the CellTracks®b Analyzer II System and three of those colors are dedicated to detecting epithelial cells and leukocytes only one channel remains available for additional biomarker analysis. However there exists a need, especially in the pharmaceutical industry, in detecting multiple biomarkers on a captured target and would prefer that the detection occur on the same target. The present invention allows for the removal of the fluorescent signals from the biomarkers and dyes which are attached to captured targets and a re-staining of the same targets with additional markers of interest. A drying step after the initial scan of the cartridge fixes the targets of interest in their original location within the cartridge so that when the cartridge is re-stained those same targets are easily found and analyzed for the presence of the additional biomarkers of interest.

In the first step of the procedure, a CellTracks® cartridge is processed on the Celltracks® Autoprep® System and Celltracks® Analyzer II System, where the captured targets are scanned and the presence of desired targets identified for location within the cartridge determined. The liquid in the cartridge is removed by aspiration and the cartridge is air dried overnight. The aspiration and air drying is done while the cartridge remains in the original MagNest®. This step "fixes" the targets, usually cell such as CTC's, in place on the cartridge so they become essentially immobile and affixed to the imaging surface at the location where they were originally detected. The preferred method of fixing the cells is to air dry the cartridge, however other fixation methods may be used and, in fact, may be required to expose some types of antigens or achieve optimal reactivity of certain antibodies with their antigens. This drying step or active fixation enables the cartridge to be removed from the MagNest® and enables the cartridge to be processed with little or no cell movement or loss. Thus allowing an imaging device such as, but not limited to, Celltracks® Analyzer II System to re-acquire the targets during subsequent analysis. The second step in the procedure exposes the cartridge to intense light generated by, but not limited to, LEDs in order to bleach the fluorescence of the dyes and markers that were attached to the targets during their initial processing. Photobleaching is effective when a fluorochrome is excited at a high rate. The wavelength band that a dye is excited in with high efficiency is typically narrow (10-50 nm). LED's efficiently generate light in a narrow wavelength band with high efficiency and are available in emission from near UV to IR. The LED efficiency is further enhanced by a heat sink. An optional homogenizer consisting of reflective or refractive surfaces can be used to improve uniformity of the light distribution on the sample. With the current prototype LED bleacher photobleaching a bright dye may take up to 20 minutes. However, 10 to 15 minutes is sufficient for dimmer signals. During the final step, the sample in the cartridge is re-stained with additional biomarkers of interest conjugated to fluorochromes. The staining solution is removed and replaced with a nuclei acid dye solution, such as CellFix containing DAPI, and the cartridge is re-analyzed on the imaging device.

FIG. 1A confirms the integrity of the sample after drying. After the sample has been dried the ferrofluid distribution and location of the targets remain the same as when the initially scanned on the CellTracks® Analyzer II System. FIG. 1B shows that the cells remain intact and in the same location both before and after drying.

FIG. 2 demonstrates the ability to re-stain in the cartridge after drying. Here, target cells were added into blood, prepared using CellSave preservative (Immunicon Corporation) and stored overnight. The sample was then processed in the CellTracks® Autoprep® System and CellTracks® Analyzer II System using a CTC kit which labels the cells with C11-PE. In the initial scan, the FITC channel remains empty as there was no marker conjugated to FITC. After the cartridges were dried and the fluorescent signal bleached, the sample was re-stained with C11-FITC in the cartridge then re-scanned on the CellTracks® Analyzer II System. The sample is now positive in both the PE and FITC channels. Although the samples were initially stained with C11-PE, there remain sufficient binding sites for subsequent C11-FITC binding.

FIGS. 3A and 3B demonstrate the ability to bleach away the fluorescent signal using light emitting diodes (LEDs). Cells were spiked into blood, preserved using CellSave preservative, and stored overnight. The sample was then processed on the CellTracks® Autoprep® System using a CTC kit which labels the cells with C11-PE. Cartridges were then scanned on the Celltracks® Analyzer II System. After aspirating the liquid and cartridge drying, the CellFix was added back to the cartridge; the cartridge was removed from the MagNest®, and then exposed to the light from the LEDs for up to 20 minutes. The cartridge was placed back into the MagNest®, the CellFix was aspirated, and the cells were re-stained with C11-FITC and then DAPI. This re-staining is necessary so that the spiked cells can be re-acquired and analyzed on the Celltracks® Analyzer II System. Bleaching was observed only for the initial C11-PE staining. After samples were scanned on the Celltracks® Analyzer II System, they were assessed for staining intensity brightness using software that determines mean fluorescence intensity (MFI).

FIG. 3A shows the bleaching of SKBR cells which stain brightly with C11-PE. After 20 minutes of bleaching the PE MFI drops from ~4000 to near 0. FIG. 3B shows the bleaching of PC3-9 cells which stain dimmer for C11-PE, typical of CTCs. The PE MFI drops from a range of 500-2000 to 0 after bleaching for 10-15 minutes.

The ultimate goal is to re-stain with a marker not previously used on the CellTracks® Autoprep® System during the initial processing of the sample. The images in FIG. 4 demonstrate the ability to take CTCs processed on the CellTracks® Autoprep® System using the dye combinations of DAPI, CD45 APC, and C11-PE, bleaching away those signals, and then re-staining cells with DAPI, C11-FITC, and p-AKT PE. AKT is a kinase important in cell signaling via the PI3K pathway. The enzyme is activated by phosphorylation, and is known to be constitutively activated in some tumors.

FIG. 4A shows the initial scan of SKBR cells captured from blood and stained on CellTracks® Autoprep® System with C11-PE. Note the negative FITC channel. FIG. 4B shows the sample after bleaching and re-stain with C11-FITC. Note the negative PE channel signal. FIG. 4C shows the sample after bleaching and re-stain with C11-FITC and pAKT-PE.

The present invention allows for the interrogation of CTCs with multiple fluorescent biomarkers of interest that would not normally be possible using a single processing protocol in the CellTracks® Autoprep® System and CellTracks® Analyzer II System. It achieves this by bleaching away the fluorescent signal of the dyes used during the initial run and re-staining in the cartridge with additional fluorescent biomarkers which can now be re-scanned using the same fluorescent channels.

The present invention considers multiple re-bleaching of the same sample with subsequent re-staining. The present invention further considers the bleaching process and its use on multiple specific binding partner assays on the same cell(s). Accordingly, multiparameter analysis of cells can be performed without having to add fluorescent channels; more filters, more light sources, and increase the complexity of the instrument and software collecting and analyzing the data. Consequently, it expands the capability of an existing 4 color fluorescent analyzer to perform 'N' parameter analysis without complex and expensive system modifications. It also allows a user to identify cartridges of interest, dry or fix them, and then store them for later high value analysis.

The invention provides for the use of the same high sensitivity fluorophore for two or more analytes on the same cell which is not possible by any other technology in the art. For example, PE has high absorption and fluorescence quantum yield which makes it well suited for detecting high sensitivity markers such as IGF-1R and p-AKT. These markers are at such a low concentration in target cells that if the antibody conjugate is coupled to FITC instead of PE, they would not be detectable. There is just not enough IGF-1R on a positive cell to provide a detectable signal using FITC due to its lower sensitivity and quantum yield. The same is true for p-AKT, however, in the present invention a CTC can be identified using CK-PE. The CK-PE signal is bleached to 0, re-stained with anti-IGF-1R-PE and IGF-1R status of the same cell determined. The IGF-1R signal can be further bleached to 0 and re-stained in the cartridge again using anti-p-AKT-PE. This process allows for all three analytes to be assayed on the same cell using the most sensitive fluorochrome available.

The invention also allows for additional high value research or clinical information be collected on samples, without having to call patients back in and collect additional samples. If CTCs, or other targets of interest, are found, the sample can be prepared using the present invention and the properties of those CTCs examined and explored without having to subject the patient to additional invasive procedures. Also if the sample is found to not contain the target of interest, additional high value tests, procedures, and reagents do not have to be consumed. This is different than other methods where the test reagents must be added before it is known whether the sample actually contains the target of interest.

The present invention further considers subsequent FISH analysis on the same cells to look for gene amplifications, translocations, or breaks that may correlate with or explain the observed expressions. The preferred means for subsequent FISH analysis incorporates the use of repeat-free probes (U.S. Ser. No. 12/067,532).

The invention allows for detailed analysis of CTCs or other targets of interest once found. This can be used during drug development to identify whether an individual's CTCs are likely to be susceptible to targeted drug therapies. It can then be used to further explore or confirm drug mechanism studies by determining whether intracellular or other markers are up regulated, down regulated, or phosphorylated in response to therapies as predicted from in vitro studies, thus providing for companion diagnostics. The presents invention has utility in providing a minimal invasive method to obtain samples for determining a patient's suitability for targeted personalized medicine. Other applications known in the art such as, but not limited to, detection of activation states of leukocyte subsets important in inflammatory damage, or interleukin storms such as septic shock. The present method is also useful as a research use only (RUO) service, and possibly ultimately as a product that could be run at hospital and reference laboratories.

While certain of the preferred embodiments of the present invention have been described and specifically exemplified above, it is not intended that the invention be limited to such embodiments. Various modification may be made thereto without departing from the spirit of the present invention, the full scope of the improvements are delineated in the following claims.

We claim:

1. A method for confirming the detection and enumeration of circulating tumor cells in a mixed cell population, comprising:
   a. obtaining a biological specimen from a test subject, said specimen comprising the mixed cell population suspected of containing said circulating tumor cells;
   b. isolating said circulating tumor cells by immunomagnetic enrichment;
   c. identifying said circulating tumor cells by a multiparametric profile analysis where said profile is obtained through steps comprising:
      i. labeling said circulating tumor cells with a first fluorescent marker, wherein the fluorescent labeled marker comprises a label of a high sensitivity fluorophore and a first marker that has a low concentration on said circulating cells;
      ii. scanning said circulating tumor cells;
      iii. aspirating the fluid from said circulating cells wherein said aspirating fixes said circulating cells in position on an imaging surface;
      iv. photobleaching the fluorescently labeled circulating tumor cells of step (i) using light-emitting diodes;
      v. labeling said circulating tumor cells in step (iv) with a second fluorescent labeled marker wherein said second fluorescent labeled marker comprises the same label of step (i) and a second marker wherein the second marker has a low concentration in said circulating tumor cell; and
      vi. rescanning said fluorescently labeled circulating tumor cells of step (v); and
   d. confirming said circulating tumor cells when the first and second fluorescent labeled markers are associated with the circulating tumor cells.

2. The method of claim 1 wherein said profile analysis is genotypic.

3. The method of claim 1 where said profile analysis is phenotypic.

4. The method of claim 1 wherein said label comprising the high sensitivity fluorophore is phycoerythrin.

5. The method of claim 1 wherein said first marker that has a low concentration is insulin like growth factor-1 receptor (IGF-1R).

6. The method of claim 1 wherein said second marker that has a low concentration is kinase important in cell signaling (p-AKT).

\* \* \* \* \*